United States Patent [19]
Inary et al.

[11] Patent Number: 5,712,412
[45] Date of Patent: Jan. 27, 1998

[54] PROCESS FOR PRODUCING HIGHLY PURE TEREPHTHALIC ACID

[75] Inventors: Masato Inary; Fumio Ohkoshi; Fumiya Zaima, all of Kurashiki, Japan

[73] Assignees: Mitsubishi Gas Chemical Co., Inc., Tokyo; Toyo Boseki Kabushiki Kaisha, Osaka; Mizushima Aroma Company, Ltd., Kurashiki, all of Japan

[21] Appl. No.: 562,764

[22] Filed: Nov. 27, 1995

[30] Foreign Application Priority Data

Dec. 26, 1994 [JP] Japan ................................. 6-321950

[51] Int. Cl.$^6$ ................................................ C07C 51/42
[52] U.S. Cl. ........................ 562/485; 562/412; 562/486
[58] Field of Search ........................... 562/412, 485, 562/486

[56] References Cited

U.S. PATENT DOCUMENTS

| | | | |
|---|---|---|---|
| 4,201,871 | 5/1980 | Tanouchi et al. | 562/486 |
| 5,008,450 | 4/1991 | Yamamoto et al. | 562/485 |

FOREIGN PATENT DOCUMENTS

| | | |
|---|---|---|
| 0 321 272 | 6/1989 | European Pat. Off. . |
| 2 014 985 | 9/1979 | United Kingdom . |

*Primary Examiner*—Samuel Barts
*Attorney, Agent, or Firm*—Frishauf, Holtz, Goodman, Langer & Chick, P.C.

[57] ABSTRACT

There are disclosed a method for replacing a dispersion medium wherein an original slurry comprising solid particles and an original dispersion medium is introduced in a dispersion medium replacement column at the top thereof, a replacing dispersion medium is introduced in the column at the bottom thereof to replace the original dispersion medium with the replacing dispersion medium, the resultant replaced slurry comprising the solid particles and the replacing dispersion medium is taken out from the column at the bottom thereof, and the original dispersion medium is taken out from the column at the top thereof, which method comprises dividing the fluid in the intermediate portion into a plurality of parallel streams, stirring the slurry in the bottom of the column to uniformize the slurry, and controlling the feed rates of the replacing dispersion medium and the replaced slurry to maintain the slurry in the bottom portion of the column at a concentration higher than that of the slurry in the intermediate portion of the column; an apparatus for carrying out the method; and a process for producing highly pure terephthalic acid from the slurry comprising an original dispersion medium and crystalline particles of terephthalic acid. The method and apparatus are capable of producing highly pure terephthalic acid at a high replacement efficiency of the dispersion medium with simplified equipment in an extremely advantageous manner.

4 Claims, 7 Drawing Sheets

PROCESS FOR PRODUCING HIGHLY PURE TEREPHTHALIC ACID

BACKGROUND OF THE INVENTION

1. Field of the Invention

The present invention relates to a method for continuously replacing a dispersion medium of solid particles with a different dispersion medium, an apparatus for carrying out the method, and a process for producing highly pure terephthalic acid by using the apparatus. More particularly, it pertains to a method for replacing a dispersion medium of solid particles with a single apparatus by continuously and efficiently transferring the solid particles form the original slurry composed of the solid particles and the original dispersion medium in the upper layer of the apparatus to a different dispersion medium to be fed in the lower layer of the apparatus by taking advantage of the gravity settling phenomenon of the solid particles; an apparatus for replacing the original dispersion medium for the purpose of carrying out the method; and a process for producing highly pure terephthalic acid by using the apparatus.

As specific examples of a process for producing terephthalic acid, the present invention relates to a method for replacing the original dispersion medium of crude terephthalic acid slurry which has been obtained by liquid-phase oxidation reaction with a different replacing dispersion medium, and to a method for replacing the original dispersion medium of purified terephthalic acid slurry which has been obtained by catalytic hydrogenation treatment or recrystallization treatment of crude terephthalic acid with a different replacing dispersion medium.

2. Description of Related Arts

The procedure of replacing an original dispersion medium in the original slurry composed of solid particles and the aforesaid original dispersion medium with a different dispersion medium signifies that two procedures in the conventional method in which the aforesaid original dispersion medium is firstly separated away from the aforesaid original slurry, and thereafter a different replacing dispersion medium is added to the aforesaid solid particles to slurry the particles again, are unified into single procedure. Such unified procedure frequently appears in practical chemical industries.

In the following, the explanation of the solid particles will be focused on those of terephthalic acid. Terephthalic acid is produced by liquid-phase oxidation of a p-phenylene compound such as p-alkylbenzene typified by p-xylene usually in acetic acid as a solvent in the presence of a catalyst such as cobalt and manganese, or a promotor exemplified by a bromine compound and acetaldehyde.

However, the reaction product of the aforesaid reaction is in the form of crude terephthalic acid slurry in acetic acid as a solvent which slurry contains as impurities, 4-carboxybenzaldehyde (4CBA), p-toluic acid (p-TOL), benzoic acid and color causative substances. Accordingly, crude terephthalic acid which is obtained by separating and drying the above-mentioned slurry inevitably contains these impurities, which necessitates considerably advanced purification technique for the purpose of producing highly pure terephthalic acid.

As a method for purifying the crude terephthalic acid slurry obtained from the above-mentioned reaction, mention is made of the known method in which acetic acid solvent as the dispersion medium is replaced with fresh acetic acid solvent minimized in the contents of impurities and the resultant slurry is subjected to immersion treatment at a high temperature or reoxidation. In addition, as a method for purifying the crude terephthalic acid, mention is made of various known methods in which the crude terephthalic acid is dissolved in a solvent such as water, acetic acid or the mixed solvent thereof at a high temperature and high pressure and the resultant solution is subjected to the treatment by catalytic hydrogenation, decarbonization, oxidation, recrystallization or the like.

In any of the production of crude terephthalic acid by liquid-phase oxidation reaction and the purification thereof, there is finally required a procedure of separating terephthalic acid crystal from the dispersion medium.

However, 4CBA, p-TOL, benzoic acid and color causative substances that are present as impurities, in the crude terephthalic acid slurry obtained by liquid-phase oxidation or in the slurry formed by purification treatment of the crude terephthalic acid, are almost dissolved in the dispersion medium at a high temperature, but when any of the slurries is cooled to about 100° C. to form a slurry containing terephthalic acid crystal, these impurities are incorporated into the terephthalic acid crystal, thereby making it difficult to produce highly pure terephathalic acid.

Therefore, in order to separate terephthalic acid having a purity as high as possible from the dispersion medium contained in the crude terephthalic acid slurry after the oxidation reaction or in the slurry formed after the purification treatment of the crude terephthalic acid, it is necessary to separate the terephthalic acid under the conditions of a high temperature and high pressure.

On the other hand, the most prevailing method for separating a dispersion medium from a slurry containing a crystal is centrifugal separation method, which is widely used also in the case of separating terephthalic acid slurry.

The centrifugal separation method is characterized in that a slurry is introduced into a basket rotating at a high speed to allow separated dispersion medium to overflow at the upside, and to direct separated crystals towards the underside. It is known, however, that a continuous operation of a centrifugal separator at a high temperature and pressure is accompanied by several difficulties arising from the restriction on the constitution and function of the centrifugal separator.

In the first place, crystal rinse is difficult during and after centrifugal separation and thus, the amount of dispersion medium stuck to the crystal is apt to increase. In order to eliminate the problem, a method in which the centrifugally separated terephthalic acid crystal in the form of cake is reslurried by means of fresh hot solvent is usually put into practice. However, the problem of necessitating separation procedure a couple of times repeatedly in this method still remains unsolved. Furthermore, the high-speed rotation at a high temperature and pressure results in troublesomeness and difficulty in the maintenance and preservation of the centrifugal separator, whereby the investment cost thereof is undesirably increased. In view of the foregoing, it can not be said that the centrifugal separation is a state-of-the-art technique in the field of solid/liquid separation.

There has recently been proposed a dispersion medium replacement apparatus which takes advantage of gravity settling of terephthalic acid crystal as a method taking the place of centrifugal separation method. (For example, refer to Japanese Patent Application Laide-Open Nos.53431/1982 (EP 0321272), 87744/1980(GB 2014985), etc.) According to Japanese Patent Application Laid-Open No.53431/1982 (EP 0321272), the dispersion medium replacement apparatus is equipped inside with horizontal trays each having a plurality of holes. It is explained therein that unless such a structure is equipped, the replacement efficiency is not so high as that expected because of channelling or back mixing of the fluid inside the apparatus. Likewise, there is described in Japanese Patent Application Laid-Open No. 87744/1980 (GB 2014985) that trays which form slant faces are installed to contrive the improvement in replacement performance of the apparatus.

In the case of dealing with a slurry, especially in the case of dispersion medium replacement taking advantage of gravity settling, the installation of such trays is accompanied by serious difficulties such as deposit or accumulation on the trays, clogging of openings, bulking, etc., thereby requiring much labor for stabilizing the operation. Thus, the installation of the perforated trays is far from a state-of-the-art technique.

In view of the foregoing, it is a general object of the present invention to provide a method capable of efficiently subjecting an original slurry comprising the crystalline particles of terephthalic acid and an original dispersion medium as principal components to gravity settling and dispersion medium replacement without equipping the inside of a dispersion medium replacement column, with a tray or the like, while a replacing dispersion medium is injected at the bottom of the lower zone of the column, and of finally producing highly pure terephthalic acid as the objective product.

SUMMARY OF THE INVENTION

As a result of intensive research and investigation accumulated by the present inventors in order to solve the problems and attain the object, it has been proved surprisingly that the replacement efficiency is drastically improved even with a dispersion medium replacement column without any tray by installing a stirring unit at the bottom of said column; properly controlling the feed rate of the replacing dispersion medium and the discharge rate of the replaced slurry each at the bottom of the column; and setting the concentration of the slurry at the bottom to a concentration higher than that in the intermediate part of the column.

It has been customary in the prior arts to contrive to maintain the inside of the apparatus (column) in a state as static as possible to avoid back mixing in the case of stepless structure in such a type of apparatus. Thus it was a complete surprise that stirring enhanced the replacement efficiency even though the stirring was limited to the bottom portion.

The present invention is summarized as follows.

1) A method for replacing a dispersion medium wherein an original slurry comprising solid particles and an original dispersion medium is introduced in a dispersion medium replacement column at the top portion thereof, a replacing dispersion medium is introduced in said column at the bottom portion thereof to replace the original dispersion medium contained in the original slurry with the replacing dispersion medium, the resultant replaced slurry comprising the solid particles and the replacing dispersion medium is taken out from said column at the bottom portion thereof, and the original dispersion medium is taken out from said column at the top portion thereof, which method comprises stirring the internal slurry in the bottom portion of said column to maintain the slurry as uniform as possible, and controlling the feed rate of the replacing dispersion medium and the discharge rate of the replaced slurry so as to maintain the internal slurry in the bottom portion of said column at a concentration higher than that of the internal slurry in the intermediate portion of said column.

2) The method according to the above-mentioned method for replacing a dispersion medium, wherein the internal fluid in the intermediate portion of said column is divided into a plurality of parallel streams of the fluid.

3) An apparatus for replacing a dispersion medium which comprises a dispersion medium replacement column comprising a top chamber, a bottom chamber and an intermediate chamber, said top chamber being equipped with an introduction section for an original slurry comprising solid particles and an original dispersion medium, and a takeout section for the original dispersion medium; said bottom chamber being equipped with an introduction section for a replacing dispersion medium, a takeout section for a replaced slurry comprising the solid particles and the replacing dispersion medium, control sections for the feed rate of the replacing dispersion medium and the discharge rate of the replaced slurry, and a stirring unit for internal fluid in said bottom chamber; said intermediate chamber forming a passageway which allows the top chamber and the bottom chamber to vertically communicate with each other.

4) The apparatus according to the above-mentioned apparatus for replacing a dispersion medium, wherein said intermediate chamber is composed of a plurality of passages that are densely arranged parallel to each other.

5) A process for producing a highly pure terephthalic acid which comprises introducing an original slurry comprising crystalline particles of terephthalic acid and an original dispersion medium as principal components into a dispersion medium replacement column at the top portion thereof; introducing a replacing dispersion medium into said column at the bottom portion thereof; replacing the original dispersion medium contained in the original slurry with the replacing dispersion medium; taking out the original dispersion medium from said column at the top portion thereof; stirring the internal fluid in the bottom portion of the column to form a slurry as uniform as possible; controlling the feed rate of the replacing dispersion medium and the discharge rate of the replaced slurry so as to maintain the internal fluid in the bottom portion of said column at a concentration higher than that of the internal fluid in the intermediate portion of said column; taking out the replaced slurry comprising the crystalline particles of terephthalic acid and the replacing dispersion medium as principal components from said column at the bottom portion thereof; and separating said particles from the replaced dispersion medium; said original slurry having been obtained by liquid-phase oxidizing a p-phenylene compound having, at the para-position, a carboxyl group and/or a substituent group liable to be oxidized to form a carboxyl group, to form a crude slurry of terephthalic acid and regulating the resultant crude slurry to 120° to 180° C. by depressurizing and temperature lowering, or obtained by dissolving crude terephthalic acid obtained by separation from said crude slurry of terephthalic acid, in water, acetic acid or a mixed solvent theory under a high temperature and a high pressure to purify the terephthalic acid, and regulating the purified acid to 120° to 220° C. by depressurizing and temperature lowering.

6) The process for producing a highly pure terephthalic acid according to the above-mentioned process, wherein the internal fluid in the intermediate portion of said column is divided into a plurality of parallel streams of the fluid.

DESCRIPTION OF PREFERRED EMBODIMENT

Figure 1:
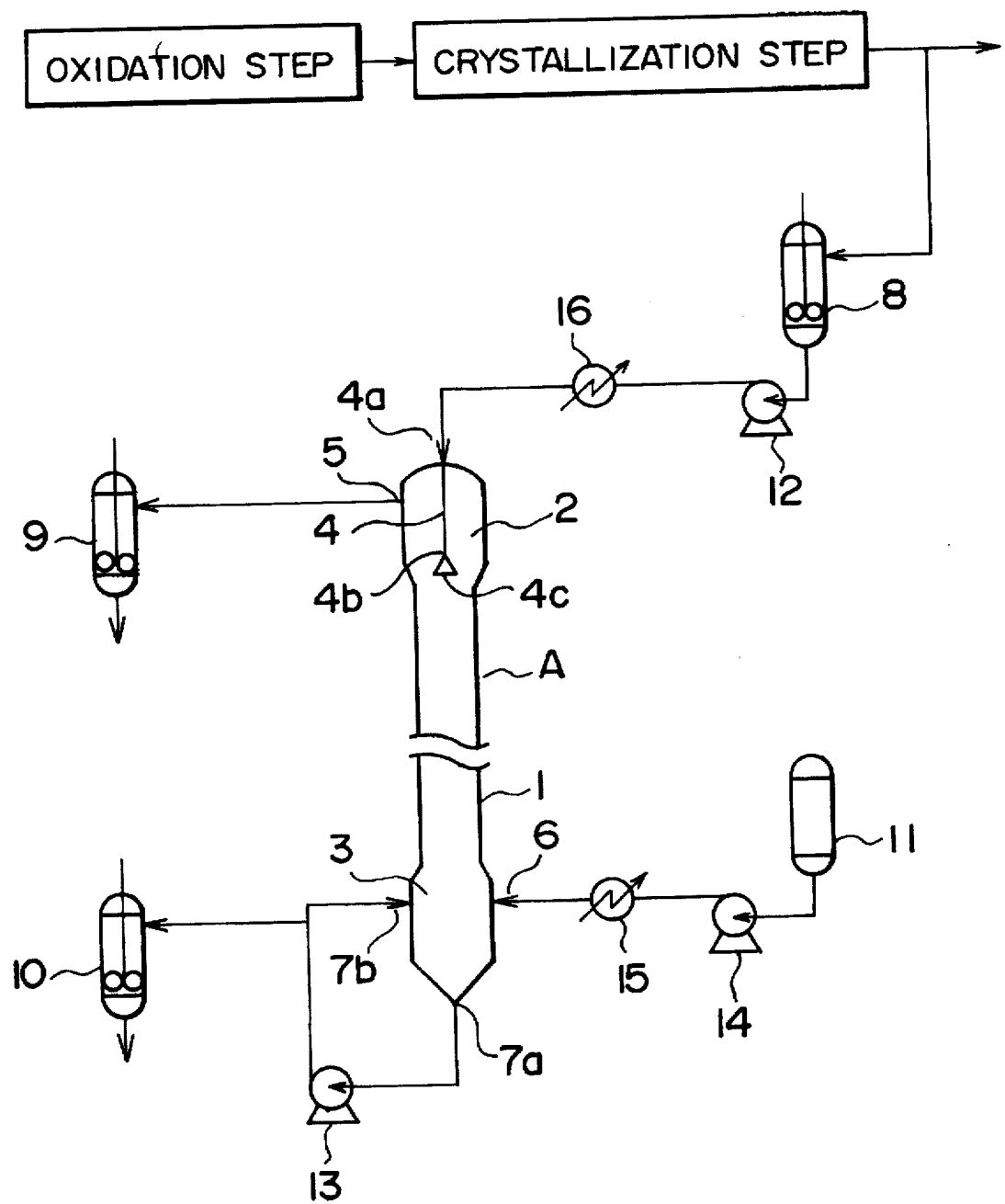
FIG.1 is an example showing simplified equipment and process flow diagram for producing highly pure terephthalic acid wherein the apparatus for replacing a dispersion medium according to the present invention is installed on the downstream side of the crystallization step of crude terephthalic acid in the case of producing highly pure terephthalic acid according to Example 1.

The method for replacing a dispersion medium according to the first aspect of the present invention comprises the steps of introducing an original slurry comprising solid particles and original dispersion medium into the dispersion medium replacement column of non-step type at the top thereof; introducing a replacing dispersion medium which is another dispersion medium, into the column at the bottom portion thereof to bring both of the dispersion media in fluid form into liquid-liquid contact, while transferring the solid particles from the original dispersion medium to the replacing dispersion medium by means of gravity settling; taking out the resultant replaced slurry comprising the solid particles and the replacing dispersion medium from the column at the bottom portion thereof; and taking out the original dispersion medium therefrom at the top portion thereof.

In the method according to the present invention, there is formed a stable state of density gradient in the column, when a highest slurry density is attained in the bottom portion of the column. In the following, description will be given of the necessity for a stable state of density gradient in the column.

It is naturally desirable to continuously carry out the dispersion medium replacement from the viewpoint of operational efficiency. In the case of performing continuous operation, however, it is necessary to carry out the discharge of concentrated slurry containing replacing dispersion medium simultaneously with the charge of the replacing dispersion medium at the bottom of the column. Thus, there is a tendency of causing nonuniform state such as partially low slurry concentration. In such a state, the intermediate portion of the column containing a slurry of a high concentration (high density) is placed above the bottom portion thereof containing a slurry of partially low concentration (low density), whereby an extremely unstable system will be formed. As a result, remarkable migration takes place between the slurry in the intermediate portion and the slurry in the bottom portion. At the same time, such migration is apt to incorporate the original slurry being in a state of liquid-liquid contact into the intermediate portion, thus making it impossible to exhibit the normal dispersion medium replacement function.

As a method for solving such a problem in the bottom portion of the column, there has been incorporated in the present method, a mixing stirring procedure which rapidly brings both the replaced slurry and the replacing dispersion medium each in the bottom portion into a state as uniform as possible. However, such incorporation of the procedure brings about the turbulence of the concentrated slurry which contains replacing dispersion medium and begins subsiding, and thus has never heretofore been inferred in the dispersion medium replacement procedure taking advantage of gravity settling phenomenon.

The stirring method in the bottom portion of the column is not specifically limited, but is exemplified by an internally stirring method by using an agitation blade in the bottom portion and an externally stirring method in which circulation piping is installed outside the bottom portion, and replaced slurry and replacing dispersion medium are taken out from the column and are returned to the bottom portion. In the case of installing circulation piping, there is preferably adoptable a method in which a stirring unit by means of an agitation blade may be allowed to intervene in the course of circulation.

Here, it is important to prevent the stirring from influencing the stability of the slurry in the intermediate portion. Thus, there is adoptable, as a simple method, a method in which the step in the intermediate portion is prolonged, a method in which the feed line of the replacing dispersion medium or the return line of the aforesaid circulation is placed as low as possible on the bottom portion of the column or the like method without specific limitation.

In the present invention, in order to suppress the above-mentioned back mixing encountered in the case of the conventional stepless structure, it is indispensable to control the feed rate of the replacing dispersion medium as well as the discharge rate of the replaced slurry in the bottom portion so as to always maintain the slurry in the bottom portion at a concentration (density) higher than that of the slurry in the intermediate portion.

The aforesaid feed rate and discharge rate in terms of liquid component are almost the same in stable operation. An excessive feed rate or discharge rate increases the liquid flow rate of the replacing dispersion medium as compared with the crystal flow rate, thus lowering the density in the bottom portion with the possibility of lowering said density lower than that in the intermediate portion, whereas an unreasonably low feed rate or discharge rate unfavorably brings about an unreasonably high density of the replaced slurry, causing difficulty in handling the slurry and finally deteriorating the productivity.

The second aspect of the present invention relates to a method for more efficiently carrying out the first aspect of the invention, and more particularly, to a method in which the slurry in the intermediate portion of the column is divided into a plurality of parallel streams of slurry in the vertical direction.

The object of such division is mainly to extremely suppress the back mixing phenomenon as described hereinafter and additionally to prevent, as much as possible, the aforesaid stirring in the bottom portion from influencing the intermediate and top portions of the column. There are adoptable a method in which the intermediate portion is vertically partitioned, but more desirably a method in which the intermediate portion is partitioned so as to equalize the shape and area of the cross section of each partition and is preferably equipped with densely assembled passages.

The vertical division of the slurry in the intermediate portion is finally intended for sedimenting the solid particles from the original slurry in a steady state adjusted as much as possible, but it is intended, in principle, to continuously carry out the dispersion medium replacement, while suppressing back mixing as much as possible by restricting back mixing stream which is inevitable in performing the procedure to a small limited space. Conversely, when an attempt is made to conduct dispersion medium replacement in a state of wide area of the intermediate portion without dividing the portion, back mixing stream is apt to take place almost all over the intermediate portion, whereby the back mixing tends to be accelerated. Accordingly, the above-mentioned attempt is not preferable for the purpose of efficiently replacing the original dispersion medium.

In the method according to the present invention, a slight stream of replacing dispersion medium or replaced slurry is preferably constituted countercurrently to the settling solid particles, that is, towards the top portion of the column from the bottom thereof. This is a countermeasure against the diffusion of the original dispersion medium toward the bottom of the column.

The apparatus according to the present invention is simple in structure and is of closed system, thereby facilitating its operation under pressure. It is preferable that the present apparatus be operated at a temperature not higher than the boiling point under the operating pressure of each of the dispersion media.

The measure taken by the present inventors including forced stirring in the bottom portion, uniform dispersion and the formation of difference in slurry concentrations is thought to have contributed to the stabilization of the system and enhanced replacement performance.

As a result of investigation made by the present inventors, it has been clarified that the replacement performance is enhanced by vertically dividing the stream of the liquid in the intermediate portion, preferably into a same shape and area of cross section, and constituting vertical lengthly passages. The enhanced replacement efficiency by such passages is thought to be due to the structure in the intermediate portion having flow adjustment function which suppresses back mixing. However, detailed mechanism of such enhancement is still unknown.

The third aspect of the present invention provides an apparatus capable of putting the first or second aspect of the process according to the present invention into practice. The dispersion medium replacement column is roughly divided into a top chamber, a bottom chamber and an intermediate chamber. The top chamber is equipped with an introduction section for the original slurry comprising solid particles and the original dispersion medium, which section may be open to the inside wall of the top chamber, but is preferably a cylindrical introduction section which extends in the top chamber and opens thereto from the standpoint of easiness of introducing the original slurry. Further, it is preferable that the end of the opening be directed downwards because of easiness of uniform liquid-liquid contact between the original slurry and the replaced slurry.

In the case of installing a cylindrical introduction section, the location of a baffle plate for liquid dispersion (or shielding plate) in the vicinity of the end of the opening opposite to said end is effective in wide uniform feeding of the original slurry and smooth proceeding of the procedure of replacing dispersion medium.

The top chamber is equipped further with a takeout section for the original dispersion medium, from where the original dispersion medium with low density almost free from solid particles is taken out and introduced to a prescribed treatment chamber.

The bottom chamber is equipped with the introduction section for the replacing dispersion medium, the takeout section for the slurry replaced with the replacing dispersion medium, control sections for the feed rate of the replacing dispersion medium and the discharge rate of the replaced slurry, and the stirring unit for the internal fluid in the column. The introduction section for the replacing dispersion medium is the introduction section of the liquid which becomes a new dispersion medium in replacement procedure.

Since the replacing dispersion medium is low in density, free from solid particles and thus apt to directly flow in the intermediate chamber, the introduction section is preferably open to the bottom of the bottom chamber.

The takeout section for the slurry replaced with the replacing dispersion medium is preferably positioned in the vicinity of the bottom of the bottom chamber so as not to give rise to turbulence of the replaced slurry.

The control for the feed rate of the replacing dispersion medium and the discharge rate of the replaced slurry makes it possible to control the density of the replaced slurry in the bottom chamber. Accordingly, importance is attached to the installation of the control sections which control both the flow rates. Thus, the control for the feed rate of the replacing dispersion medium and for the discharge rate of the liquid component in the replaced slurry exerts influence on the density of the slurry in the bottom chamber and the relative relationship with the density of the slurry in the intermediate chamber and consequently, the control is related to the dispersion medium replacement efficiency and the productivity of the replaced slurry.

The bottom chamber is equipped further with the stirring unit for internal slurry in said chamber, which is intended to uniformize, as much as possible, the dispersion state of the slurry in said chamber. The object of the uniformization resides in the prevention of unstabilization, etc. of the density gradient between the intermediate portion and the bottom chamber, which unstabilization is due to the partially decreased density of the slurry in the bottom chamber. The necessity of such prevention is as already explained.

The stirring unit is not specifically limited, but may be equipped, in the bottom chamber, with an ordinary stirrer having an agitation blade, and preferably with a baffle for the purpose of accelerating the stirring. As mentioned hereinbefore, there is preferably adoptable, as an alternative method, a method in which circulation piping is installed outside the bottom chamber, and the internal fluid in the bottom portion is taken out and returned to bottom portion, and a method in which a stirring unit by means of an agitation blade is allowed to intervene in the course of circulation.

Next, the intermediate chamber, which is a passageway allowing the top chamber and the bottom chamber to vertically communicate with each other, is preferably composed of a plurality of parallel passages densely arranged, and further a lengthy passageway, as is disclosed in the fourth aspect of the invention. The preferable embodiment of the passageway need only be composed of a plurality of parallel lengthly passages with partition walls that are vertically arranged inside, irrespective of the shape of the cross section. The partition may be in the form of any of tubular, honeycomb and grating, but it is preferable that each of the passages has a same shape and area of cross section, however, the embodiment of each passage is not limited thereto.

The cause of enhanced replacement efficiency by installing such narrow passages is not yet certain, but is presumed to be the function of suppressing the back mixing which takes place over the wide range of the cross section of the replacement column in the case of lacking such passages and also the function of adjusting the stream of fluid in the intermediate portion. Moreover, the vertical lengthy passage way, which is of vertical tubular structure without any tray or the like, is advantageous in that there is no need of being anxious about the accumulation of crystal particles and clogging in the apparatus based on such accumulation as is usually the case with a tray column.

Although the apparatus which makes use of the apparatus according to the third or fourth aspect of the present invention is simple in structure and is of closed system, thereby facilitating its operation under pressure, it is preferable that said apparatus be operated at a temperature not higher than the boiling point under the operating pressure of each of the dispersion media. In the case of operating said apparatus, the temperature of the replacing dispersion medium may be the same as or different from the temperature of the original slurry to be fed, but is preferably lower than that of the latter, since a stabilized system can be formed by the result that the density of the slurry in the bottom chamber becomes higher than the density of the original slurry to be fed.

The process for producing highly pure terephthalic acid according to the fifth aspect of the present invention relates to the process which comprises the steps of introducing an original slurry comprising crystalline particles of terephthalic acid and original dispersion medium into a dispersion medium replacement column of non-step at the top thereof; introducing a replacing dispersion medium which is intended for replacing the original dispersion medium into the column at the bottom thereof to bring both the dispersion media in fluid form into liquid-liquid contact, while transferring the crystalline particles of terephthalic acid from the original dispersion medium to the replacing dispersion medium by means of gravity settling; taking out the original dispersion medium from the column at the top portion thereof; and taking out the replaced slurry comprising the crystalline particles of terephthalic acid and the replacing dispersion medium from the column at the bottom thereof.

The original slurry to be dealt with in the fifth aspect of the present invention, which is the slurry obtained by regulating the crude slurry resulting from the liquid-phase oxidation reaction to 120° to 180° C. by depressurizing and temperature lowering, or by dissolving the crude terephthalic acid obtained by separation from said crude slurry in water, acetic acid or a mixed solvent thereof under a high temperature and a pressure to purify the terephthalic acid, and regulating the purified acid to 120° to 220° C. by depressurizing and temperature lowering, comprises crystalline particles of terephthalic acid and the original dispersion medium. The principal component of the dispersion medium which constitutes the original slurry is the liquid-phase oxidation reaction solvent or the purifying treatment solvent.

There is used acetic acid, water, etc., preferably water-containing acetic acid in general as a dispersion medium in the liquid-phase oxidation reaction; and water, acetic acid, etc., preferably water in general in purify treatment.

On the other hand, the replacing dispersion medium may be the same as the original dispersion medium of the original slurry, that is, the substance same as the liquid-phase oxidation reaction solvent or purifying treatment solvent or a composition containing the same or may be a substance different from any of the aforesaid solvents or a composition. Usually, water, acetic acid or the mixture thereof is used as the replacing dispersion medium.

According to the apparatus or method of the present invention, in the case where the original dispersion medium is acetic acid, the replacement of the acetic acid with water brings about the above-mentioned purification effect; and besides the present invention can preferably dispense with the conventional procedures in which in order to subject the liquid-phase oxidation reaction slurry to catalytic hydrogenation treatment, the procedure of precipitating crude terephthalic acid crystal is carried out by depressurizing the liquid-phase oxidation reaction liquid and lowering the temperature through the evaporation of the dispersion medium, and thereafter the resultant crude terephthalic acid is separated, dried and again dissolved in the solvent for catalytic hydrogenation treatment.

The replacing dispersion medium to be used is subjected to the removal of impurities contained therein to the extent that at least the purification effect through the replacement is realized.

The dispersion medium replacement column is operated at a slurry concentration of 1 to 50%, preferably 3 to 20% by weight in the intermediate portion, at a slurry concentration of 1 to 50%, preferably 10 to 40% by weight and at a slurry concentration not lower than that of the intermediate portion in the bottom portion of the column. In this case, the above-described flow rate to be controlled can not be numerically specified as a specific range, but need only be such a flow rate as maintaining the density in the bottom port at a density not lower than that in the intermediate portion thereof. The form or shape of terephthalic acid particles which is the object of the present invention is not specifically limited.

As the original slurry to be dealt with in the fifth aspect of the present invention, there is used crude terephthalic acid slurry which is obtained by the liquid-phase oxidation reaction, or the slurry which is obtained by dissolving the crude terephthalic acid obtained by separation from said crude slurry in water, acetic acid or a mixed solvent thereof under a high temperature and a pressure to purify the terephthalic acid and then lowering the pressure and temperature. Since high dispersion medium replacement efficiency is obtained by carrying out the dispersion medium replacement using the method of the first and second aspects of the present invention and the apparatus of the third and fourth aspects of the present invention, highly pure refined terephthalic acid is obtained according to the fifth aspect of the present invention.

The sixth aspect of the present invention relates to a method for more efficiently carrying out the fifth aspect of the invention, and more particularly, to a method in which the slurry containing terephthalic acid crystal in the intermediate portion of the column thereof according to the fifth aspect thereof is divided into a plurality of parallel streams of slurry in the vertical direction.

As described in the second aspect of the invention, the object of such division is mainly to extremely suppress the back mixing phenomenon and additionally to prevent, as much as possible, the aforesaid stirring in the bottom portion from influencing the intermediate portion of the column. There are adoptable a method in which the intermediate portion is vertically partitioned, but more desirably a method in which the intermediate portion is partitioned so as to equalize the shape and area of the cross section of each partition and is preferably equipped with densely assembled passages.

The vertical division of the slurry in the intermediate portion is finally intended for sedimenting the solid particles from the original slurry in a steady state adjusted as much as possible, but it is intended, in principle, to continuously carry out the dispersion medium replacement, while suppressing back mixing as much as possible. Conversely, when an attempt is made to conduct dispersion medium replacement without dividing the portion, back mixing stream is apt to take place almost all over the intermediate portion, whereby the back mixing tends to be accelerated. Accordingly, the above-mentioned attempt is not preferable for the purpose of efficiently replacing the original dispersion medium.

In the method according to the present invention, a slight stream of replacing dispersion medium or replaced slurry is preferably constituted contercurrently to the settling solid particles of terephthalic acid crystal, that is, towards the top portion of the column from the bottom thereof.

The first to sixth aspects of the present invention have been described in detail hereinbefore. The method and apparatus according to the present invention exhibit such working effect that the method and apparatus are widely applicable to the dispersion medium replacement for a crystal-containing slurry, and in particular, are preferably usable in the case of producing highly pure terephthalic acid by replacing, with another replacing dispersion medium, a crude terephthalic-acid slurry obtained from liquid-phase oxidation reaction or a refined terephthalic-acid slurry obtained from catalytic hydrogenation or the like of crude terephthalic acid.

Thus, it can be said that the method and apparatus for replacing dispersion medium are each a novel developing technique which has imparted replacing function to gravity thickening method.

In the following, the present invention will be described in more detail with reference to non-limitative examples and comparative examples. The examples relate to the production of highly pure terephthalic acid on the basis of liquid-phase oxidation reaction. Specifically, Examples 1 and 4 and Comparative Examples 1 and 3 relate to a crystallization step for crude terephthalic acid slurry obtained by liquid-phase oxidation reaction, which step is incorporated with an apparatus for replacing dispersion medium of the present invention. In Example 1 and Comparative Example 1, the apparatus comprises a dispersion medium replacement column without any partition plate in the intermediate portion thereof. Example 4 and Comparative Example 3 obey the method of the present invention wherein the slurry containing terephthalic acid crystal in the intermediate portion is divided in a plurality of parallel streams of the slurry.

Examples 2 and 3 and Comparative Example 2 relate to a crystallization step for refined terephthalic acid after crude terephthalic acid has been catalytically hydrogenated in the refining step, which crystallization step is incorporated with an apparatus for replacing a dispersion medium according to the present invention. Example 3 relates to a method in which the fluid in the intermediate portion of the dispersion medium replacement column is divided into a plurality of parallel streams of the fluid.

EXAMPLE 1

The apparatus for replacing dispersion medium as illustrated in FIG. 1 comprises a dispersion medium replacement column A as the main apparatus, an original slurry tank 8 for storing the original slurry to be fed to the column, a replacing dispersion medium tank 11 for storing the medium to be fed to the column, an overflow dispersion medium tank 9 for receiving replaced original dispersion medium, a replaced slurry tank 10 for receiving the discharged replaced slurry and liquid feed and stirring pumps 12, 13 and 14.

The dispersion medium replacement column A is a stainless steel-made cylindrical column having 100 mm inside diameter and vertically long tubular structure. The column is equipped with a top chamber 2 which forms an introduction chamber for original slurry from outside at the upper end side (top portion) thereof and a bottom chamber 3 which forms a discharge chamber for replaced slurry to outside at the lower end side (bottom portion) thereof. Inside the top chamber 2 is inserted an introduction unit for the original slurry 4 which comprises a receiver port for the original slurry 4a that is connected to an original slurry tank 8 and an introduction port for the original slurry 4b that extends to the lower portion of the top chamber and is equipped with a shielding plate 4c assisting slurry dispersion at the end thereof. The original slurry comprising an original dispersion medium and terephthalic acid crystal is transferred from the original slurry tank 8 to the introduction unit for the original 4 via an original slurry transfer pump 12 and is sprinkled inside the top chamber 2.

Most of crystalline particles of terephthalic acid in the original slurry thus sprinkled settle in the cylindrical column 1. Particularly fine particles which form a part of the crystalline particles and the original dispersion medium overflow in an overflow dispersion medium tank 9 from an original dispersion medium overflow part 5 at the upper part of the side of the chamber 2.

To the bottom chamber 3 is connected a stirring pump 13, which stirs the internal fluid in the bottom chamber 3 through the circulating flow which starts from a replaced slurry takeout unit 7a and reaches a cycle return port 7b by the pump 13. The replaced slurry is taken out from the chamber 3 through a branched line via a discharge port of the pump 13, and the replaced slurry thus taken out is stored in a replaced slurry tank 10. A replacing dispersion medium is fed in the column 1 at a replacing dispersion medium feed port 6 at the lower part of the side of the chamber 3 from a replacing dispersion medium tank 11 via a replacing dispersion medium transfer pump 14.

By the use of the above-described apparatus there was conducted an experiment for the replacement of the original dispersion medium in the crude terephthalic acid crystal slurry produced by liquid-phase oxidation reaction with a fresh acetic acid containing water. The original slurry comprising crystalline particles of terephthalic acid and an original dispersion medium had been produced by air oxidation of p-xylene in a water-containing acetic acid as a solvent by the use of a commercial scale apparatus. After the oxidation reaction in the presence of manganese acetate, cobalt acetate and hydrobromic acid as oxidation catalysts in an oxidation step, and original slurry as the starting material for the above-mentioned experiment was formed by collecting the crude terephthalic acid crystal slurry which had been subjected to temperature lowering finally to 90° C. through a crystallization step. As a result, the original slurry had a concentration of the crystalline particles of terephthalic acid of 30% by weight, a concentration of water in the dispersion medium of 11% by weight and a manganese concentration of 364 ppm.

First of all, the terephthalic acid crystal was fed in the chamber 3, in which was fed a fresh acetic acid containing water by 11% by weight, while it was heated to 180° C. by passing through a heat exchanger 15 with the pump 14, an stirring was started by actuating the pump 13 to disperse the crystal to attain a crystal concentration of 30% by weight. When the fluid level in the column 1 reached the port 5, the pump 12 was actuated to start original slurry feeding, and at the same time takeout of the replaced slurry into the tank 10 was started. The original slurry as the starting material was heated to 180° C. through a heat exchanger 16.

The feed rates and discharge rates were as follows:
Feed rate of the original slurry 40.0 kg/hr
Feed rate of the replacing dispersion medium 33.4 kg/hr
Discharge rate of the overflow dispersion medium 34.2 kg/hr
Discharge rate of the replaced slurry 39.2 kg/hr The operation was continued for several hours until the flow of the fluid in the system reached a sufficiently steady state, when the fluid in the tank 10 was analyzed. As a result, the manganese concentration in the dispersion medium was 30 ppm and accordingly, the replacement efficiency of the dispersion medium was 92%. At that time, the slurry concentration was 8% by weight in the intermediate portion of the column 1, and 30% by weight in the chamber 3 (refer to Table 1).

COMPARATIVE EXAMPLE 1

Figure 2:
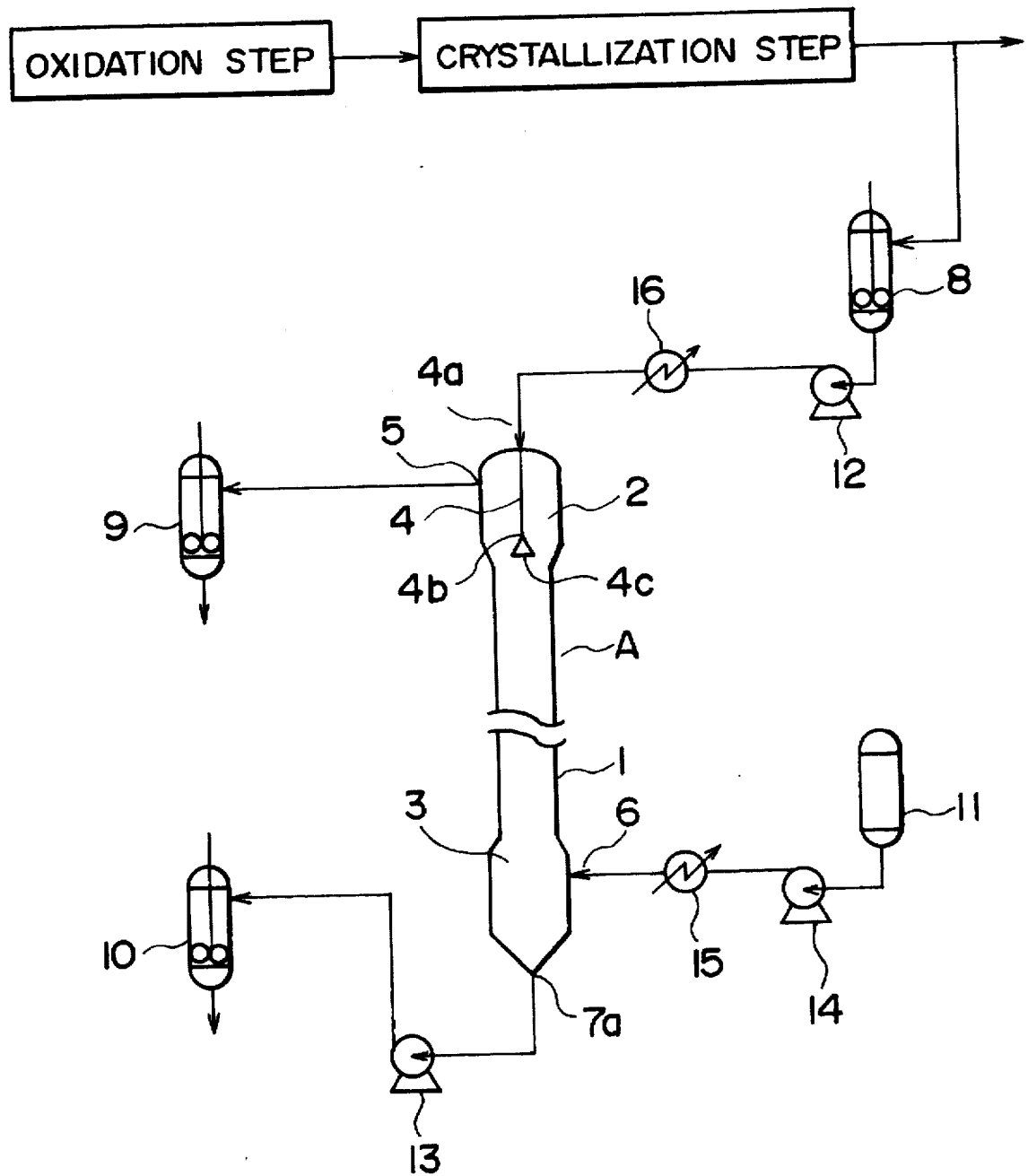
FIG.2 is an example showing simplified equipment and process flow diagram for producing highly pure terephthalic acid wherein the apparatus for replacing a dispersion medium which lacks mixing stirring between the replaced slurry and the replacing dispersion medium is installed on the downstream side of the crystallization step of crude terephthalic acid in the case of producing highly pure terephthalic acid according to Comparative Example 1.

As illustrate in FIG. 2, the procedure in Example 1 was repeated by the use of the apparatus in Example 1 except that the slurry taken out from the replaced slurry takeout unit 7a was wholly discharged into the tank 10 without circulating the slurry by pump circulation. As a result, the manganese concentration in the fluid in the tank 10 was 100 ppm and thus, replacement efficiency of the dispersion medium was 73%. At that time, the slurry concentration was 8% by weight in the intermediate portion of the column 1 and 3% in the chamber 3 (refer to Table 1).

EXAMPLE 2

Figure 3:
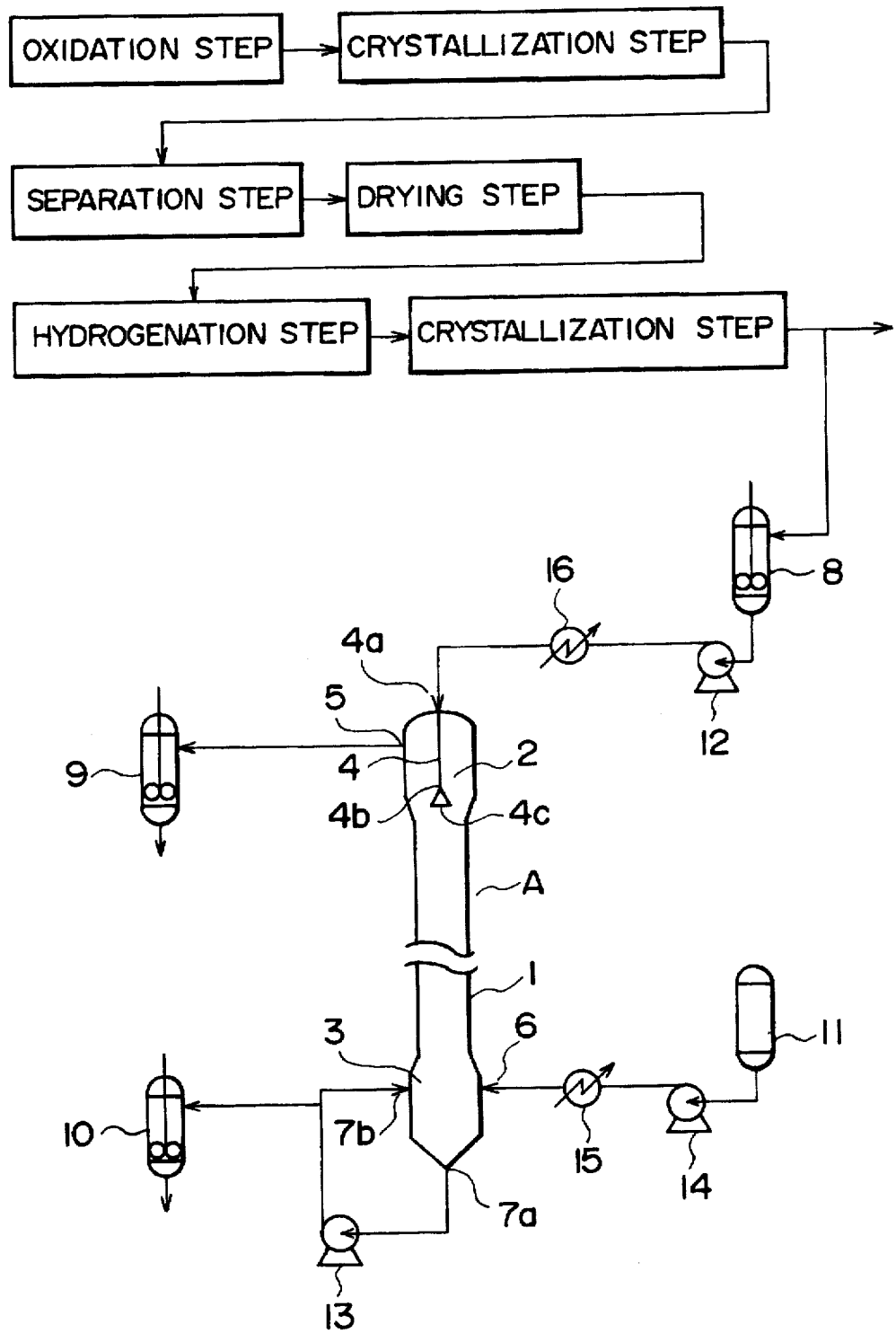
FIG.3 is an example showing simplified equipment and process flow diagram for producing highly pure terephthalic acid wherein the apparatus for replacing a dispersion medium according to the present invention is installed on the downstream side of the crystallization step of purified terephthalic acid which step follows catalytic hydrogenation treatment in the purification step of the crude terephthalic acid in the case of producing highly pure terephthalic acid according to Example 2.

As illustrated in FIG. 3, by the use of the apparatus for replacing dispersion medium as used in Example 1 there was conducted an experiment for the replacement of the dispersion medium of refined terephthalic acid slurry, with fresh water, said slurry being produced by refining crude terephthalic acid through catalytic hydrogenation and recrystallization in a solvent, said crude terephthalic acid being produced by air oxidation of p-xylene in the presence of cobalt, manganese and bromine as catalysts. The original slurry to be used had been produced, through the use of a commercial scale apparatus, by air-oxidizing p-xylene in a water-containing acetic acid in the presence of manganese acetate, cobalt acetate and hydrobromic acid as oxidation catalysts; crystallizing the reaction product; then separating and drying the crystal to form crystalline particles of terephthalic acid; dissolving the particles in hot water; catalytically hydrogenating the impurities in the resultant solution in the presence of hydrogen and palladium catalyst supported on activated carbon; then crystallizing the particles; and subsequently cooling the particles to 100° C.

First of all, the refined terephthalic acid crystal was fed in the chamber 3, in which was fed a fresh water, while it was heated to 150° C. by passing through the heat exchanger 15 with the pump 14, an stirring was started by actuating the pump 13 to disperse the crystal to attain a crystal concentration of 30% by weight. When the fluid level in the column 1 reached the port 5, the pump 12 was actuated to start original slurry feeding, and at the same time, takeout of the replaced slurry into the tank 10 was started. The original slurry as the starting material was heated to 150° C. through the heat exchanger 16.

The feed rates and discharge rates were as follows:
Feed rate of the original slurry 40.0 kg/hr
Feed rate of the replacing dispersion medium 33.4 kg/hr
Discharge rate of the overflow dispersion medium 34.2 kg/hr
Discharge rate of the replaced slurry 39.2 kg/hr The dispersion medium in the slurry introduced in the column contained 240 ppm of benzoic acid as an impurity.

The operation was continued for several hours until the flow of the fluid in the system reached a sufficiently steady state, when the fluid in the tank 10 was analyzed. As a result, the benzoic acid concentration in the dispersion medium was 20 ppm and accordingly, the replacement efficiency of the dispersion medium was 92%. At that time, the slurry concentration was 6% by weight in the intermediate portion of the column 1, and 30% by weight in the chamber 3 (refer to Table 1).

COMPARATIVE EXAMPLE 2

Figure 4:
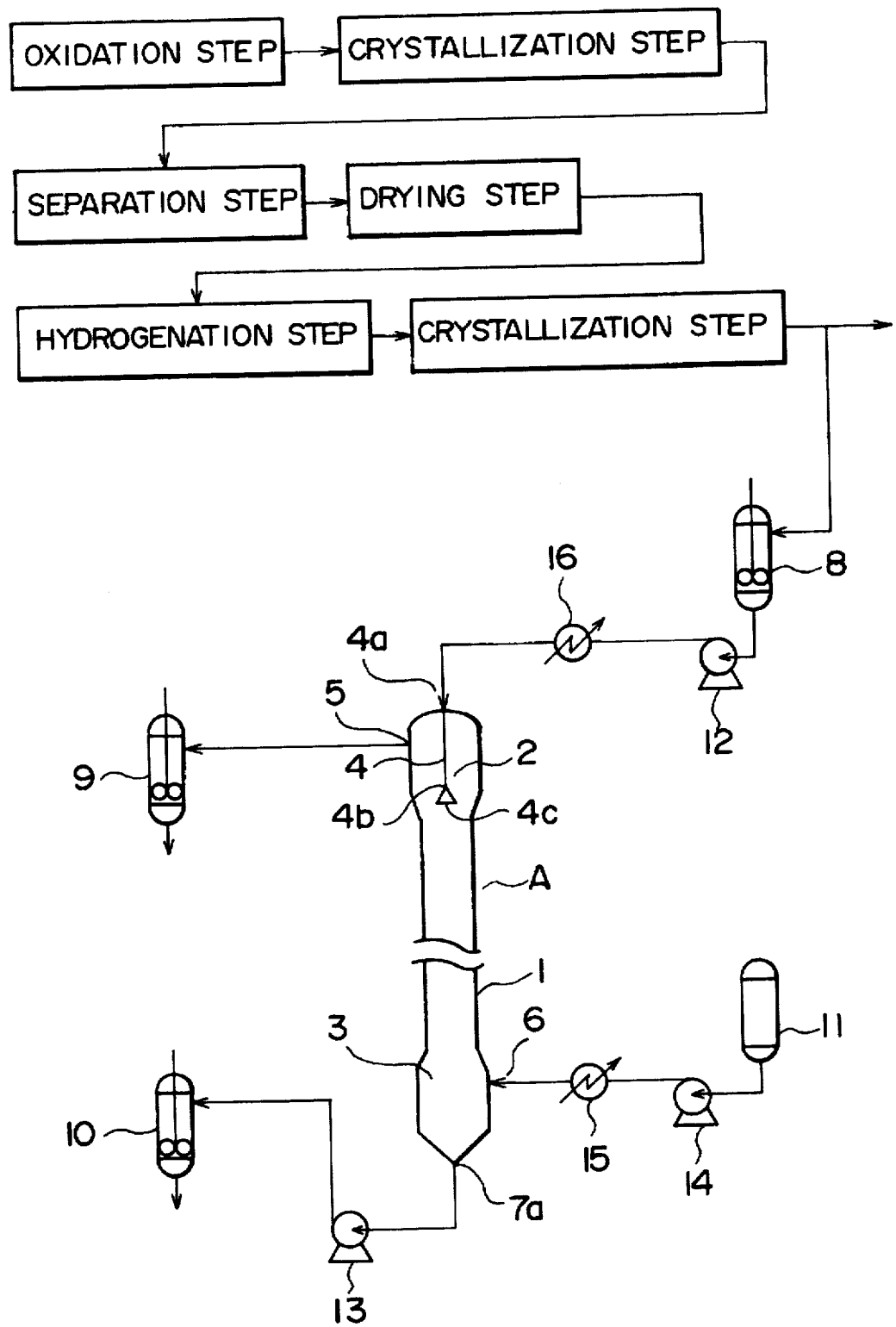
FIG.4 is an example showing simplified equipment and process flow diagram for producing highly pure terephthalic acid wherein the apparatus for replacing a dispersion medium which lacks a mixing stirring between the replaced slurry and the replacing dispersion medium, is installed on the downstream side of the crystallization step of purified terephthalic acid which step follows catalytic hydrogenation treatment in the purification step of the crude terephthalic acid in the case of producing highly pure terephthalic acid according to Comparative Example 2.

As illustrated in FIG. 4, the procedure in Example 1 was repeated by the use of the apparatus in Example 1 except that the slurry taken out from the replaced slurry takeout unit 7a was wholly discharged into the tank 10 without circulating the slurry by pump circulation and that the slurry used was the same as that used in Example 2.

As a result, the benzoic acid concentration in the fluid in the tank 10 was 70 ppm and thus, the replacement efficiency of the dispersion medium was 71%. At that time, the slurry concentration was 6% by weight in the intermediate portion of the column 1 and 3% in the chamber 3 (refer to Table 1).

EXAMPLE 3

Figure 5:
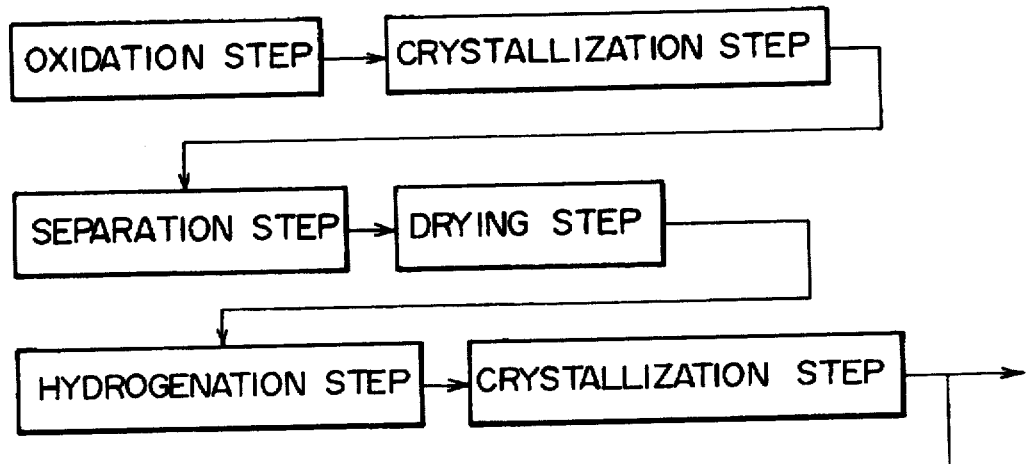
FIG.5 is an example showing simplified equipment and process flow diagram for producing highly pure terephthalic acid wherein the apparatus for replacing a dispersion medium according to the present invention comprising a dispersion medium replacement column in which the internal fluid in the intermediate portion of said column is divided into a plurality of parallel streams of the fluid, is installed on the downstream side of the crystallization step of purified terephthalic acid which step follows catalytic hydrogenation treatment in the purification step of the crude terephthalic acid in the case of producing highly pure terephthalic acid according to Example 3.
Figure 5:
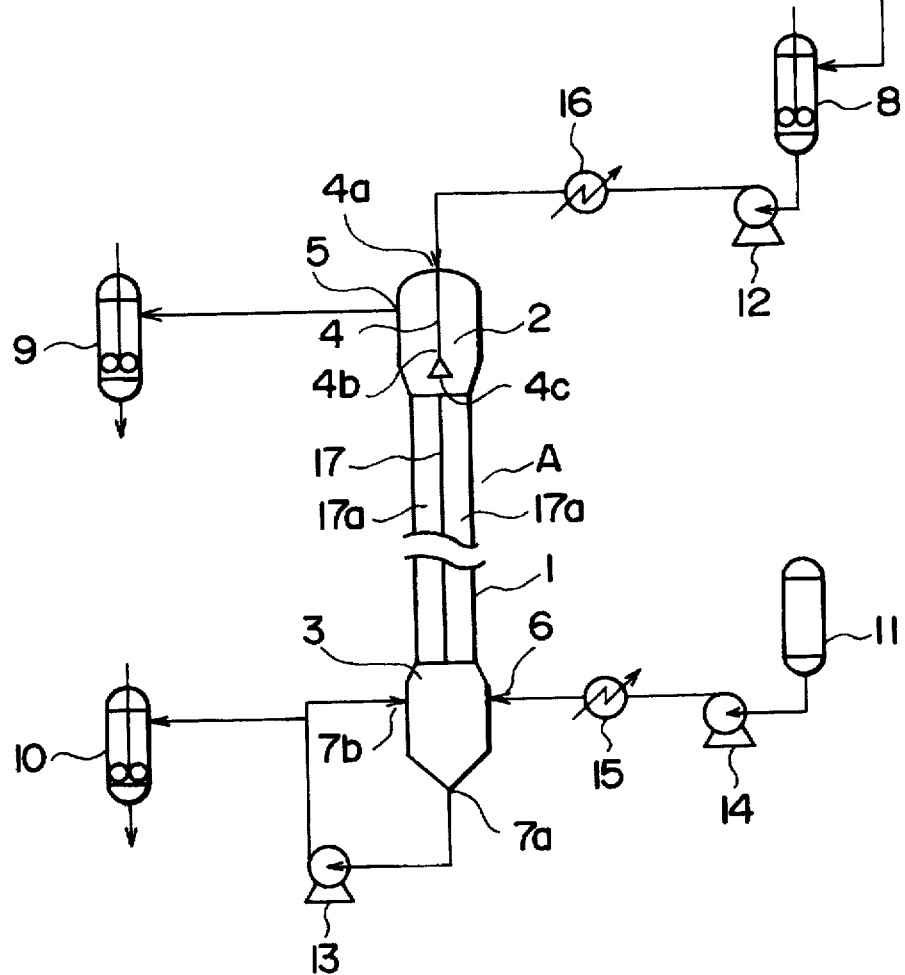
Figure 8:
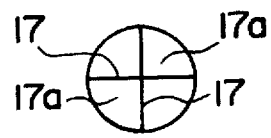
FIG.8 is a transverse sectional view of the central section of a cylindrical column equipped with a plurality of passages which column is installed in the intermediate portion of the dispersion medium replacement column which constitutes the apparatus for replacing dispersion medium to be used for carrying out the method according to the present invention.

By the use of the apparatus as shown in FIG. 5 in which the cylindrical column of the apparatus for replacing dispersion medium of FIG. 3 was incorporated inside with a vertical partition plate having a cruciform cross section (FIG. 8 illustrates the transverse cross section of the cylindrical column portion, that is, the intermediate portion in FIG. 5), the procedure in Example 2 was repeated. As a result, the benzoic acid concentration in the fluid in the tank 10 was 7 ppm and thus, the replacement efficiency of the dispersion medium was 97%. At that time, the slurry concentration was 6% by weight in the cylindrical column and 30% in the chamber 3 (refer to Table 1).

EXAMPLE 4

Figure 6:
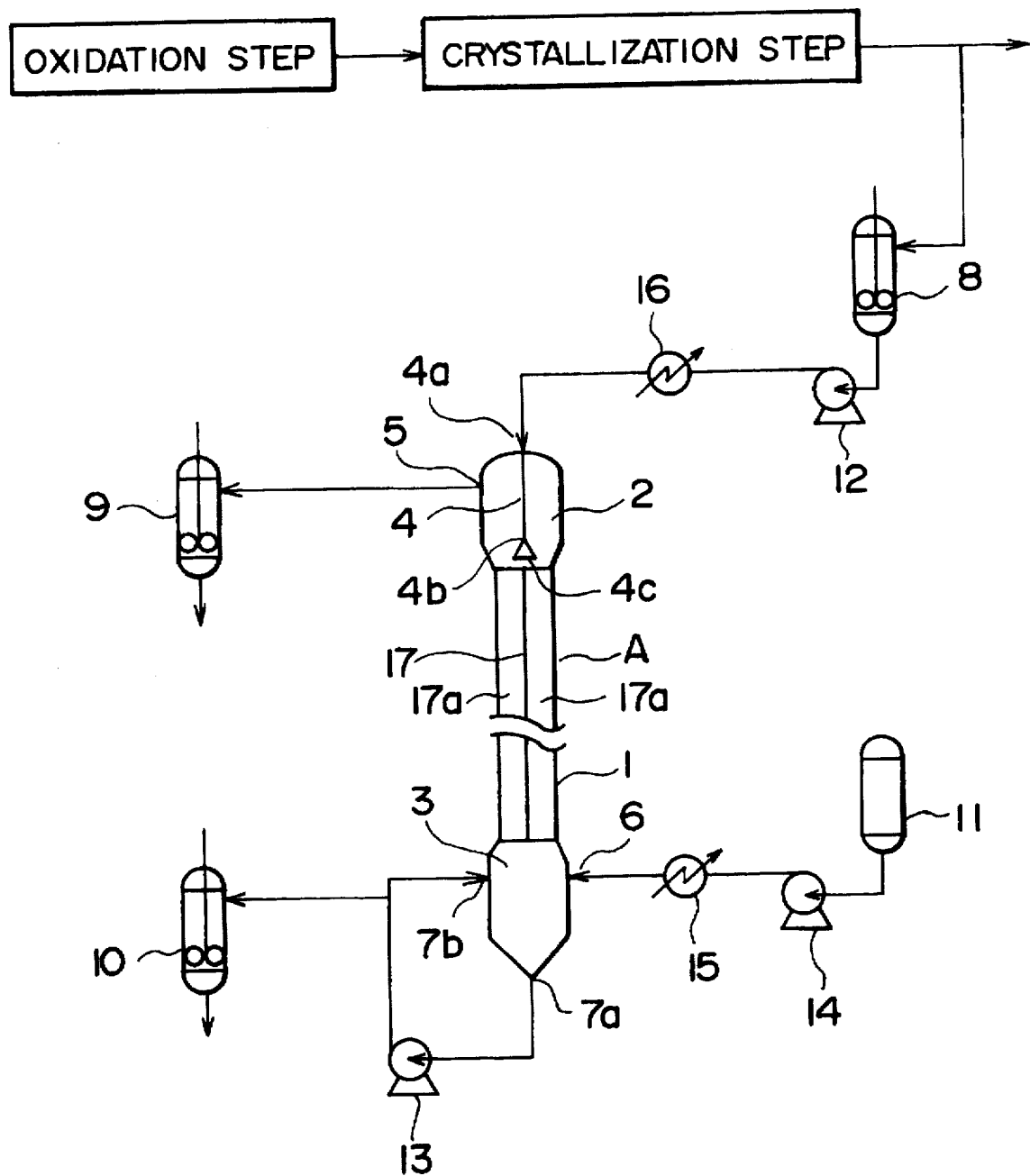
FIG.6 is an example showing simplified equipment and process flow diagram for producing highly pure terephthalic acid wherein the apparatus for replacing a dispersion medium according to the present invention comprising a dispersion medium replacement column in which the internal fluid in the intermediate portion of said column is divided into a plurality of parallel streams of the fluid, is installed on the downstream side of the crystallization step of crude terephthalic acid in the case of producing highly pure terephthalic acid according to Example 4.

As illustrated in FIG. 6, by the use of the apparatus for replacing dispersion medium, as used in Example 3, there was conducted an experiment for the replacement, with a fresh water, of the acetic acid which was the mother liquor of the original slurry of terephthalic acid that had been produced by air-oxidizing p-xylene. The original slurry to be used had been produced by using manganese acetate, cobalt acetate and hydrobromic acid as oxidation catalysts and, after the completion of the reaction, cooling the slurry to 100° C. Then, the procedure in Example 1 was repeated to proceed with the experiment except that the original slurry concentration was 30% by weight, original slurry feed temperature was 150° C., and the feed temperature of water as the replacing dispersion medium was 150° C.

The feed rates and discharge rates were as follows:

Feed rate of the original slurry 40.0 kg/hr

Feed rate of the replacing dispersion medium 33.4 kg/hr

Discharge rate of the overflow dispersion medium 34.2 kg/hr

Discharge rate of the replaced slurry 39.2 kg/hr

The operation was continued for several hours until the flow of the fluid in the system reached a sufficiently steady state, when the fluid in the tank 10 was analyzed. As a result, the acetic acid concentration in the dispersion medium was 1.8% by weight and accordingly, the replacement efficiency of the dispersion medium was 98%. At that time, the slurry concentration was 6% by weight in the intermediate portion of the column 1, and 30% by weight in the chamber 3 (refer to Table 1).

COMPARATIVE EXAMPLE 3

Figure 7:
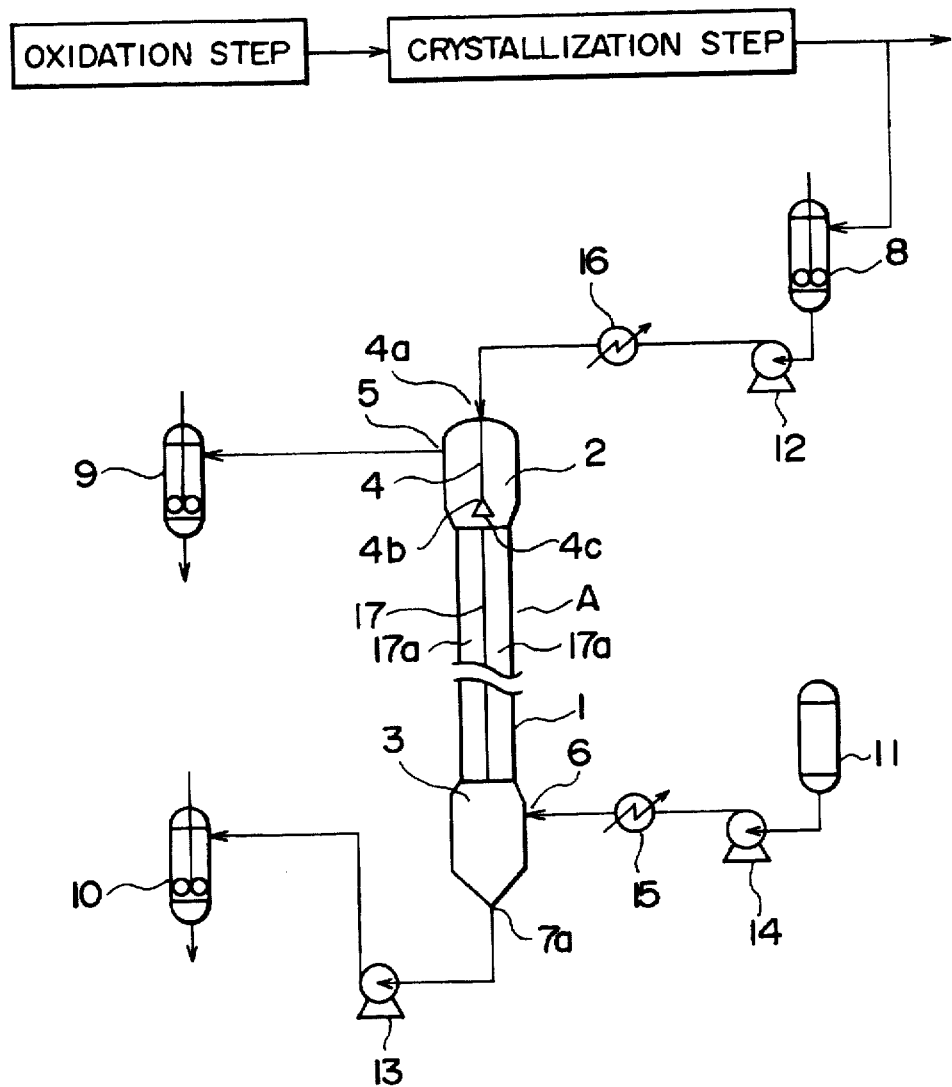
FIG.7 is an example showing simplified equipment and process flow diagram for producing highly pure terephthalic acid wherein the apparatus for replacing a dispersion medium comprising a dispersion medium replacement column in which the internal fluid in the intermediate portion of said column is divided into a plurality of parallel streams of the fluid, but mixing stirring between the replaced slurry and the replacing dispersion medium is lacking, is installed on the downstream side of the crystallization step of crude terephthalic acid in the case of producing highly pure terephthalic acid according to Comparative Example 3.

As illustrated in FIG. 7, the procedure in Example 4 was repeated by the use of the apparatus in Example 4 except that the slurry taken out from the replaced slurry takeout unit 7a was wholly discharged into the tank 10 without circulating the slurry by pump circulation. As a result, the acetic acid concentration in the fluid in the tank 10 was 35% by weight and thus, the replacement efficiency of the dispersion medium was 61%. At that time, the slurry concentration was 6% by weight in the intermediate portion of the column 1 and 3% in the chamber 3 (refer to Table 1).

TABLE 1

| Example / Comparative Example | 1 | 1 | 2 | 2 | 3 | 4 | 3 |
|---|---|---|---|---|---|---|---|
| Stirring | Yes | No | Yes | No | Yes | Yes | No |
| Partition plate | No | No | No | No | Yes | Yes | Yes |
| Original dispersion medium | acetic acid | acetic acid | water | water | water | acetic acid | acetic acid |
| Replacing dispersion medium | acetic acid | acetic acid | water | water | water | water | water |
| Concentration of slurry in column intermediate portion (%) | 8 | 8 | 6 | 6 | 6 | 6 | 6 |
| Concentration of slurry in column bottom portion (%) | 30 | 3 | 30 | 3 | 30 | 30 | 3 |
| Replacement efficiency of dispersion medium (%) | 92 | 73 | 92 | 71 | 97 | 98 | 61 |

It can be said as follows from the results of the examples and the comparative examples.

(1) The replacement efficiency of the dispersion medium is enhanced by uniformizing the fluid in the bottom chamber through the stirring of the same, and by controlling the feed rate of the replacing dispersion medium and the discharge rate of the replaced slurry so as to regulate the replaced slurry concentration to a concentration higher than that of the slurry in the replacing column. (Compare Example 1 with Comparative Example 1, Example 2 with Comparative Example 2, and Example 4 with Comparative Example 3, respectively.)

(2) The replacement efficiency of the dispersion medium is further enhanced by stirring the fluid in the bottom chamber so as to take slurry concentration gradient in the same manner as in the above-mentioned item (1) and further by installing a partition plate (partition plates) inside the cylindrical column. (Compare Examples 1 and 2 with Examples 3 and 4.)

What is claimed is:

1. A method for replacing a dispersion medium wherein an original slurry comprising solid particles and an original dispersion medium is introduced in a dispersion medium replacement column at the top portion thereof, a replacing dispersion medium is introduced in said column at the bottom portion thereof to replace the original dispersion medium contained in the original slurry with the replacing dispersion medium, the resultant replaced slurry comprising the solid particles and the replacing dispersion medium is taken out from said column at the bottom portion thereof, and the original dispersion medium is taken out from said column at the top portion thereof, which method comprises stirring the internal slurry in the bottom portion of said column to maintain the slurry as uniform as possible, and controlling the feed rate of the replacing dispersion medium and the discharge rate of the replaced slurry so as to maintain the internal slurry in the bottom portion of said column at a concentration higher than that of the internal slurry in the intermediate portion of said column.

2. The method for replacing a dispersion medium according to claim 1, wherein the internal fluid in the intermediate portion of said column is divided into a plurality of parallel streams of the fluid.

3. A process for producing a highly pure terephthalic acid which comprises introducing an original slurry comprising crystalline particles of terephthalic acid and an original dispersion medium as principal components into a dispersion medium replacement column at the top portion thereof; introducing a replacing dispersion medium into said column at the bottom portion thereof; replacing the original dispersion medium contained in the original slurry with the replacing dispersion medium; taking out the original dispersion medium from said column at the top portion thereof; stirring the internal fluid in the bottom portion of the column to form a slurry as uniform as possible; controlling the feed rate of the replacing dispersion medium and the discharge rate of the replaced slurry so as to maintain the internal fluid in the bottom portion of said column at a concentration higher than that of the internal fluid in the intermediate portion of said column; taking out the replaced slurry comprising the crystalline particles of terephthalic acid and the replacing dispersion medium as principal components from said column at the bottom portion thereof; and separating said particles from the replaced dispersion medium; said original slurry having been obtained by liquid-phase oxidizing a p-phenylene compound having, at the para-position, a carboxyl group and/or a substituent group liable to be oxidized to form a carboxyl group, to form a crude slurry of terephthalic acid and regulating the resultant crude slurry to 120° to 180° C. by depressurizing and temperature lowering, or obtained by dissolving crude terephthalic acid obtained by separation from said crude slurry of terephthalic acid, in water, acetic acid or a mixed solvent thereof under a high temperature and a high pressure to purify the terephthalic acid, and regulating the purified terephthalic acid to 120° to 220° C. by depressurizing and temperature lowering.

4. The process for producing a highly pure terephthalic acid according to claim 5, wherein the internal fluid in the intermediate portion of said column is divided into a plurality of parallel streams of the fluid.

* * * * *